US007369250B2

(12) United States Patent
Dubois et al.

(10) Patent No.: US 7,369,250 B2
(45) Date of Patent: May 6, 2008

(54) SYSTEM AND METHOD TO INSPECT COMPONENTS HAVING NON-PARALLEL SURFACES

(75) Inventors: Marc Dubois, Clifton Park, NY (US); Thomas E. Drake, Jr., Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 226 days.

(21) Appl. No.: 11/089,902

(22) Filed: Mar. 25, 2005

(65) Prior Publication Data

US 2006/0215174 A1    Sep. 28, 2006

(51) Int. Cl.
*G01B 11/02* (2006.01)
*G01B 9/02* (2006.01)
*G01N 21/00* (2006.01)

(52) U.S. Cl. .................. 356/502; 356/432; 73/657
(58) Field of Classification Search ................. 356/432, 356/502; 73/655, 657
See application file for complete search history.

(56) References Cited

U.S. PATENT DOCUMENTS

| | | | | |
|---|---|---|---|---|
| 4,581,939 A | * | 4/1986 | Takahashi | 73/643 |
| 4,633,715 A | * | 1/1987 | Monchalin | 73/657 |
| 5,148,807 A | * | 9/1992 | Hsu | 600/402 |
| 6,609,425 B2 | * | 8/2003 | Ogawa | 73/608 |
| 6,633,384 B1 | * | 10/2003 | Drake et al. | 356/432 |
| 6,684,701 B2 | * | 2/2004 | Dubois et al. | 73/579 |
| 2002/0171845 A1 | * | 11/2002 | Drake, Jr. | 356/502 |
| 2002/0171846 A1 | * | 11/2002 | Drake, Jr. | 356/503 |
| 2004/0027578 A1 | * | 2/2004 | Drake et al. | 356/502 |
| 2004/0154402 A1 | * | 8/2004 | Drake, Jr. | 73/621 |
| 2005/0023434 A1 | * | 2/2005 | Yacoubian | 250/200 |
| 2005/0099634 A1 | * | 5/2005 | Dubois et al. | 356/502 |
| 2005/0231735 A1 | * | 10/2005 | Dubois et al. | 356/614 |
| 2006/0132804 A1 | * | 6/2006 | Dubois et al. | 356/614 |
| 2006/0215174 A1 | * | 9/2006 | Dubois et al. | 356/502 |

* cited by examiner

*Primary Examiner*—Patrick Connolly
(74) *Attorney, Agent, or Firm*—Bracewell & Giuliani LLP

(57) ABSTRACT

The present invention provides a method to detect and generate ultrasonic displacements at a remote target for ultrasonic inspection. This method involves generating an ultrasonic wave at a first location on an upper surface of the remote target. This ultrasonic wave is reflected from interior surfaces within the remote target wherein the reflected ultrasonic wave produces ultrasonic displacement at a second location on the upper surface of the remote target. A detection laser beam is generated and directed to the second location on the upper surface of the remote target. Here, the detection laser beam is scattered by the ultrasonic displacements to produce phase-modulated light. This phase-modulated light is collected and processed to obtain data representative of the ultrasonic surface displacements. Further, these ultrasonic displacements, when processed, will yield inspection information associated with the interior of the remote target.

26 Claims, 10 Drawing Sheets

SYSTEM AND METHOD TO INSPECT COMPONENTS HAVING NON-PARALLEL SURFACES

RELATED APPLICATIONS

This application is related to and incorporates by reference in it entirety for all purposes U.S. Pat. No. 6,122,060 (U.S. application Ser. No. 09/345,558) entitled "METHOD AND APPARATUS FOR DETECTING ULTRASONIC SURFACE DISPLACEMENTS USING POST-COLLECTION OPTICAL AMPLIFICATION" filed on Jun. 30, 1999, and U.S. Pat. No. 6,657,733 B1 (U.S. patent application Ser. No. 09/416,399) entitled "METHOD AND APPARATUS FOR DETECTING ULTRASONIC SURFACE DISPLACEMENTS USING POST-COLLECTION OPTICAL AMPLIFICATION" filed on Oct. 12, 1999 which claims priority to and repeats a substantial portion of prior U.S. Provisional Application No. 60/091,229 filed on Jun. 30, 1998 and U.S. Provisional Application No. 60/091,240 filed on Jun. 30, 1998 to Thomas E. Drake. This application also incorporates by reference prior U.S. patent application Ser. No. 10/668,896 filed on Sep. 23, 2003 entitled "METHOD AND APPARATUS FOR DETECTING ULTRASONIC SURFACE DISPLACEMENTS USING POST COLLECTION OPTICAL AMPLIFICATION" by Thomas E. Drake and U.S. patent application Ser. No. 11/018,994 filed on Dec. 21, 2004 entitled "SYSTEM AND METHOD TO DECREASE PROBE SIZE FOR IMPROVED LASER ULTRASOUND DETECTION" to Marc Dubois, et al.

TECHNICAL FIELD OF THE INVENTION

The present invention relates generally to inspection systems, and more particularly, to a system and method for inspecting the internal structure of components fabricated from composite materials and having non-parallel surfaces.

BACKGROUND OF THE INVENTION

In recent years, the use of advanced composite materials to fabricate structures has experienced tremendous growth in the aerospace, automotive, and many other commercial industries. While composite materials offer significant improvements in performance, they require strict quality control procedures in both the manufacturing processes and after the materials are in service in finished products. Specifically, non-destructive evaluation (NDE) methods must be developed assess the structural integrity of composite materials in an efficient and cost-effective manner. This assessment detects inclusions, delaminations and porosities within the internal structure. Conventional NDE methods are slow, labor-intensive, and costly. As a result, testing procedures have historically adversely affected the manufacturing costs associated with composite structures.

Various methods and apparatuses have been proposed to assess the structural integrity of composite structures. One solution uses an ultrasonic source to generate ultrasonic surface displacements which are then measured and analyzed. Often, the external source of ultrasound is a transducer mechanically coupled to the target to be tested or a pulsed generation laser beam directed at the target. Laser light from a separate detection laser is scattered by ultrasonic surface displacements at the target. Collection optics then collect the scattered laser energy. The collection optics are coupled to an interferometer or other optical processing device to produce an output or data signal. Data about the structural integrity of the composite structure is then obtained through analysis of the scattered laser energy.

Laser ultrasound has been shown to be very effective for the inspection of composite materials during the manufacturing process. These inspections have been complicated by parts having non-uniform thickness or non-parallel surfaces. To date, laser ultrasound has been limited to parts having parallel surfaces.

During ultrasonic inspection, echoes reflected by the interior surfaces of a sample allow measuring the sample thickness. Additionally, this echo provides an indication of how to position the detection time gate. When target materials have non-parallel surfaces, the measurement of this echo becomes complicated as the ultrasonic wave does not return to the point of origin.

Unfortunately, laser ultrasound is limited to parts having parallel surfaces. The benefits associated with ultrasonic inspection cannot be applied using current techniques to parts having non-parallel surfaces. These parts constitute a significant fraction of the total composite material production, especially in the aircraft industry.

SUMMARY OF THE INVENTION

The present invention provides a system and method to perform laser ultrasound inspections on complex composite materials that substantially addresses the above-identified needs and others. More specifically, the present invention provides the ability to inspect the internal structure of objects, having non-parallel outer surfaces. One embodiment of the present invention provides a method to detect and generate ultrasonic displacements at a remote target in order to perform ultrasonic inspections. This method involves generating an ultrasonic wave at a first location on an exterior surface of the remote target. This ultrasonic wave is reflected from interior surfaces within the remote target. The reflected ultrasonic wave produces ultrasonic displacement at a second location on the exterior surface of the remote target. A detection laser beam is generated and directed to the second location on the exterior surface of the remote target. Here, scatter detection laser beam ultrasonic displacements to produce phase-modulated light. This phase-modulated light is collected and processed by both optical and signal processors to obtain data representative of the ultrasonic surface displacements. Further, these ultrasonic displacements, when processed, further yield inspection information associated with the internal structure of the remote target.

Additionally, other embodiments may involve determine the second location at the surface from the dimensions of the remote target. This may be done by a processor that calculates an expected second location on which the detection beam and collection optics may be directed or focused. The detection field of the detection laser beam may substantially overlap both the first location and the second location. Alternatively, the detection field may be directed to the second location. The overlap may be reduced to improve the overall signal-to-noise ratio (SNR). The detection field and collection field of the collection optics are primarily focused or directed to the second location. This provides the ability to inspect the internal composition of objects made of material such as composite material. The outer surfaces of the object may not necessarily be parallel. More generically, the interior surface may not necessarily be orthogonal to the generated ultrasonic wave. This means that the reflected ultrasonic wave may return to a second location differing from the point of origin of the ultrasonic wave produced at the first location.

Another embodiment may utilize a compact optical probe having a number of angled terminated fibers to direct the generation laser beam, detection laser beam, and collect phase-modulated light. The generation laser beam and detection laser beam are directed along an axis determined by facets or curved surfaces of the angled terminated fiber. The exact location of the detection, generation, and collection fields are determined by how the angled terminated fibers terminate and the geometry of the object and probe.

Another embodiment determines the second location on the surface of the remote target based upon a computer model of the remote target and the dimensions associated therewith. Alternatively, these dimensions may be determined from sensors directed at the object.

In addition to providing a methodology, other embodiments may provide a laser ultrasonic inspection system operable to detect ultrasonic displacements at a remote target. This ultrasonic inspection system includes a generation laser source, a first optical assembly, a detection laser source, a second optical assembly, collection optics, an interferometer or other optical processor, and a signal processor. The generation laser source generates the detection laser beam which the first optical assembly receives and directs to the remote target. At the remote target, the generation laser beam produces an ultrasonic wave originating from a first location at which the generation laser directs a generation field on the exterior surface of the remote target. A detection laser source generates a detection laser beam that a second optical assembly then receives and directs to the remote target where ultrasonic displacements at a second location within the detection field on the surface of the remote target scatter the detection laser beam to produce phase-modulated light. Collection optics collect the phase-modulated light which an interferometer or optical processor processes to generate an output signal. The output signal is processed to obtain data representative of ultrasonic surface displacements at the surface of the remote target, as well as inspection information representative of the internal structure of the remote target.

Yet another embodiment provides a laser ultrasonic inspection system to inspect the internal structure of an object fabricated from composite materials. This inspection system includes a number of sensors, a generation laser source, a first optical assembly, a detection laser source, a second optical assembly, collection optics, and optical and data processor(s). The sensors may detect, locate and measure the dimensions of the object. The generation laser source produces a generation laser beam which first optical assembly receives and directs to the generation field substantially located at a first location on an exterior surface of the object. The generation laser beam produces an ultrasonic wave originating from the first location. This ultrasonic wave is reflected from interior surfaces or boundaries which may not necessarily be orthogonal to the ultrasonic wave. The fact that the ultrasonic wave is not necessarily orthogonal to the interior surface will cause the reflected ultrasonic wave to be directed to and produce ultrasonic displacements at a second location that may differ from that of the first location. This location is determined, at least in part, by the geometry and acoustic properties of the object. A detection laser source generates a detection laser beam that a second optical assembly receives and directs to a detection field. The detection field is substantially located at the second location on the surface of the object. Here, ultrasonic displacements at the second location and illuminated by the detection laser beam produce phase-modulated light. The collection optics have a collection field that may substantially overlap the detection field within which the phase-modulated light is collected. Optical processor(s), such as an interferometer, and a data or signal processor(s) process the phase-modulated light and associated output signals, obtain data representative of the ultrasonic surface displacements and/or the internal structure of the object.

Other features and advantages of the present invention will become apparent from the following detailed description of the invention made with reference to the accompanying drawings.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGS., like numerals being used to refer to like and corresponding parts of the various drawings.

In general, ultrasound laser inspection is performed by having a generation laser field overlay and by a detection laser field and collection field. This approach is similar to that used when a single piezoelectric transducer (PZT) generates and detects ultrasonic waves. In parts, having walls with non-parallel surfaces or non-standard thicknesses, the ultrasonic waves are not reflected to the point of origin. Non-parallel surface(s) reflect the ultrasonic wave away from the point of origin. The direction being determined by the geometry and acoustic properties of the object. Detection by a single piezoelectric transducer may not be practical. Similarly, a laser ultrasonic inspection system overlays the detection laser beams detection field with the generation laser beams generation filed. When applied to parts having non-parallel surface or internal boundaries, the system may not detect the reflected ultrasonic wave. By producing an elliptical detection beam with a longer axis, the elliptical detection beam may cover all possible positions of the reflected ultrasonic beam and associated ultrasonic displacements.

Previous solutions have used arrays of detectors. For example, in a piezoelectric system, a single element emits an ultrasonic wave and another element of the piezoelectric transducer array detects the reflected ultrasonic wave. In such a case, the array of transducers requires the presence of ultrasonic couplant between the transducers and the part to be inspected. Additionally, the array must be kept normal to the surface sample for optimum ultrasonic inspection.

The present invention provides a detection laser illuminating a detection field and corresponding collection optics with an appropriate collection field at the sample surface larger than that of the ultrasonic generation field.

The present invention provides a detection laser that directs the detection field and an optical collection field of the corresponding collection optics having sufficient size such that the detection field and collection field are positioned where reflected interior wall echo(s) will arrive within the detection and collection fields.

Figure 1:
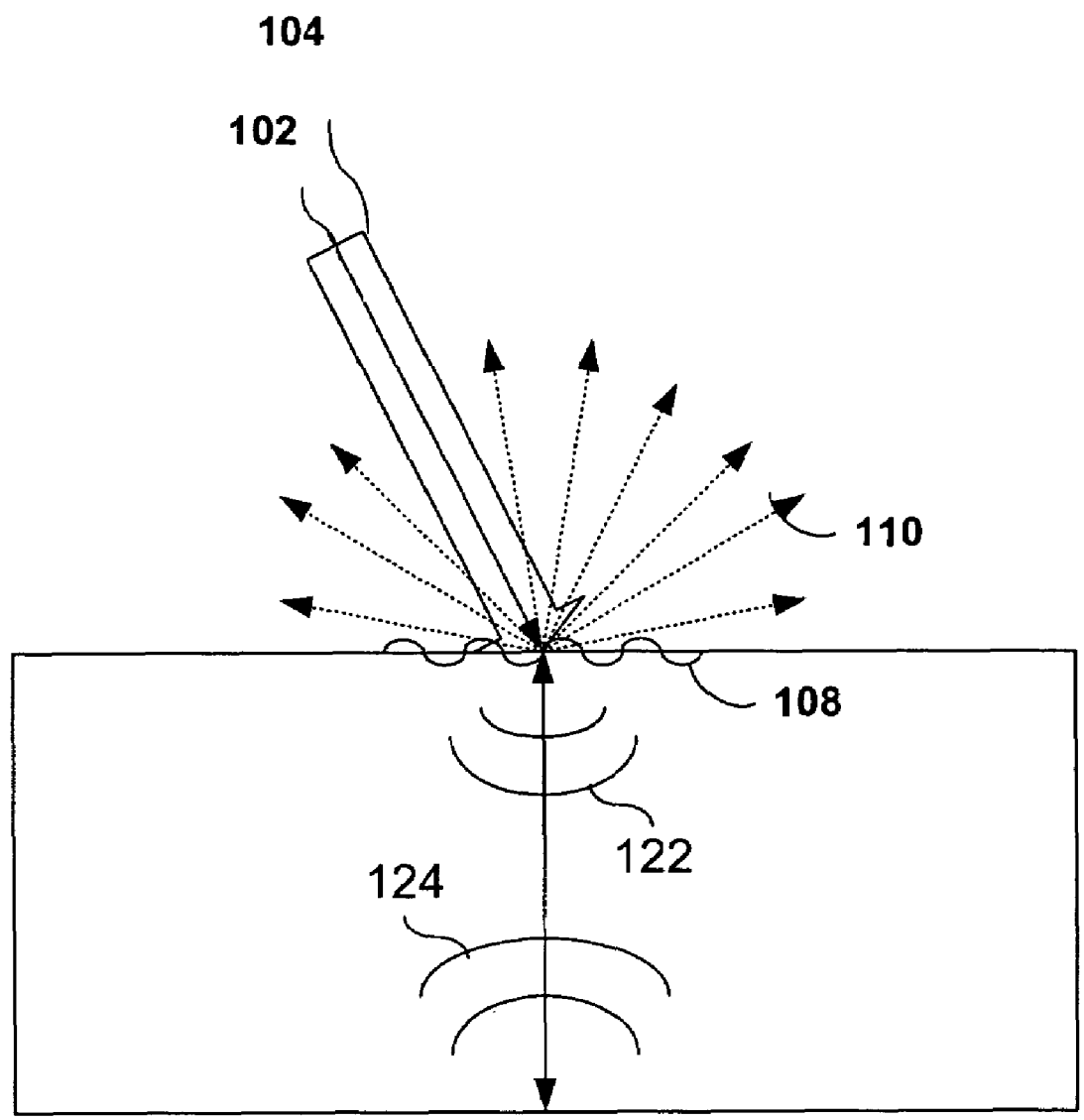
FIG. 1 illustrates the use of generation laser beam and a detection laser beam to generate and detect laser ultrasonic displacements in accordance with an embodiment of the present invention.

FIG. 1 depicts two incoming laser beams that generate and detect laser ultrasonic displacements. Laser beam 102 generates ultrasound while illumination laser beam 104 detects the ultrasound at a remote target 106, such as a composite material under test. As shown, these lasers may be coaxially applied to remote target 106 which has front surface 112 and parallel back surface 114. Generation laser beam 102 causes thermo-elastic expansion in target 106 that results in the formation of ultrasonic deformations 108. Deformations 108 modulate, scatter and reflect illumination laser beam 104 to produce phase-modulated light 110 directed away from target 106 which is collected and processed to obtain information of the internal structure of remote target 106.

Figure 2:
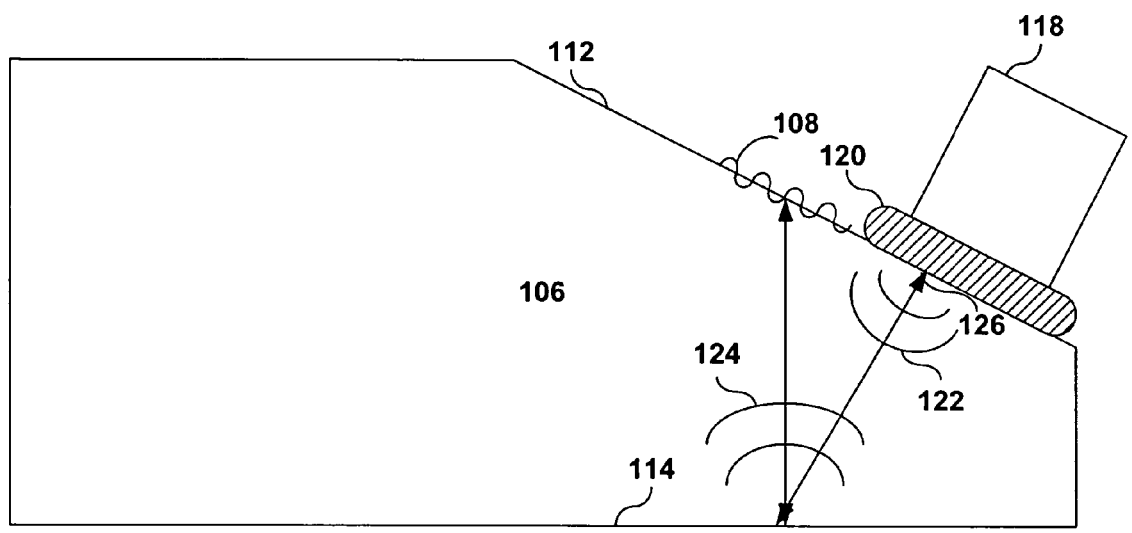
FIG. 2 illustrates problems associated with the use of a single piezoelectric transducer to generate and detect ultrasonic displacements in an object having non-parallel surfaces.

FIG. 2 depicts the problem addressed. Here, as previously encountered in the prior art, mechanical piezoelectric transducer 118 may be mechanically coupled via couplant 120 to an exterior surface 112 of remote target 106. Transducer 118 will generate ultrasonic waves 122 which are reflected off of non-parallel interior wall 114. These waves may also be reflected by boundaries and defects within the composite. Because interior surface 114 is not parallel with exterior surface 112, the reflected ultrasonic waves 124 do not return to point of origin 126. Rather, the ultrasonic deformations 108 on exterior surface 112 are located away from point of origin 126. As shown here, ultrasonic deformations 108 may be located such that they may be sensed by PZT transducer 118.

Figure 3:
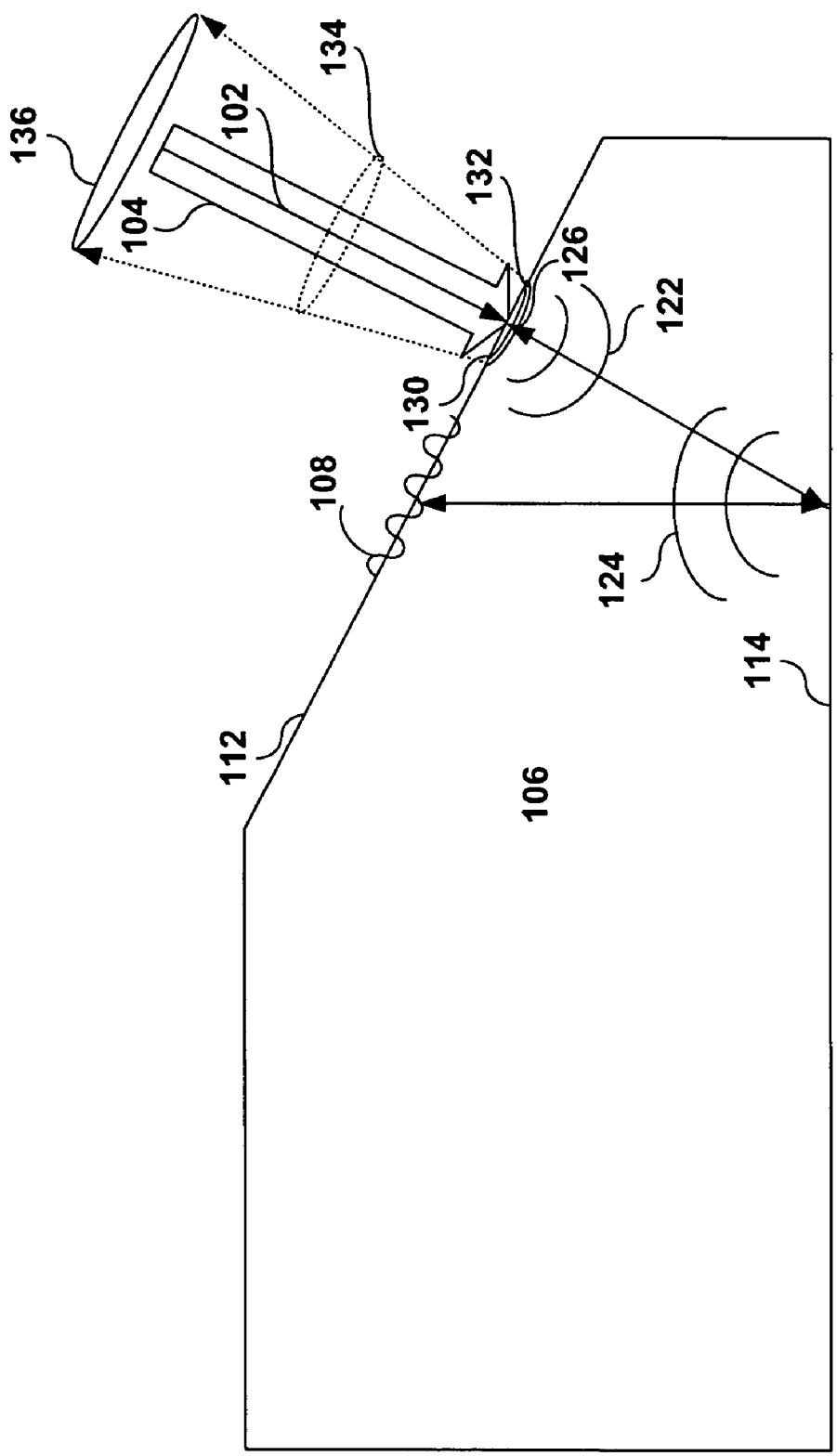
FIG. 3 illustrates problems associated with the use of a co-located generation laser beams, detection laser beams, and collection optics in generating and detecting ultrasonic displacements in an object having non-parallel surfaces.

FIG. 3 again illustrates the problem of non-parallel surfaces with remote target 106, is still encountered when a laser ultrasonic inspection system is used. There, two incoming laser beams 102 and 104 that generate and detect laser ultrasonic displacements are applied to remote target 106 wherein exterior surface 112 and exterior surface or boundary 114 are not parallel. Laser beam 102 generates an ultrasonic wave at point of origin 126 co-located with the illumination spot or generation field of generation laser 102. Detection laser 104 illuminates detection field 132. Typically, collection optics 136 are focused or directed to collect phase-modulated light 110 from detection field 134. However, because interior surface 114 is not parallel to exterior surface 112, ultrasonic wave 122 produces a reflected wave 124 that does not return to the point of origin. Thus, detection field 134 illuminated by detection laser beam 104 does not necessarily illuminate the ultrasonic displacements when ultrasonic displacements are not located within the detection field. Such displacements are not detected and processed.

Figure 4:
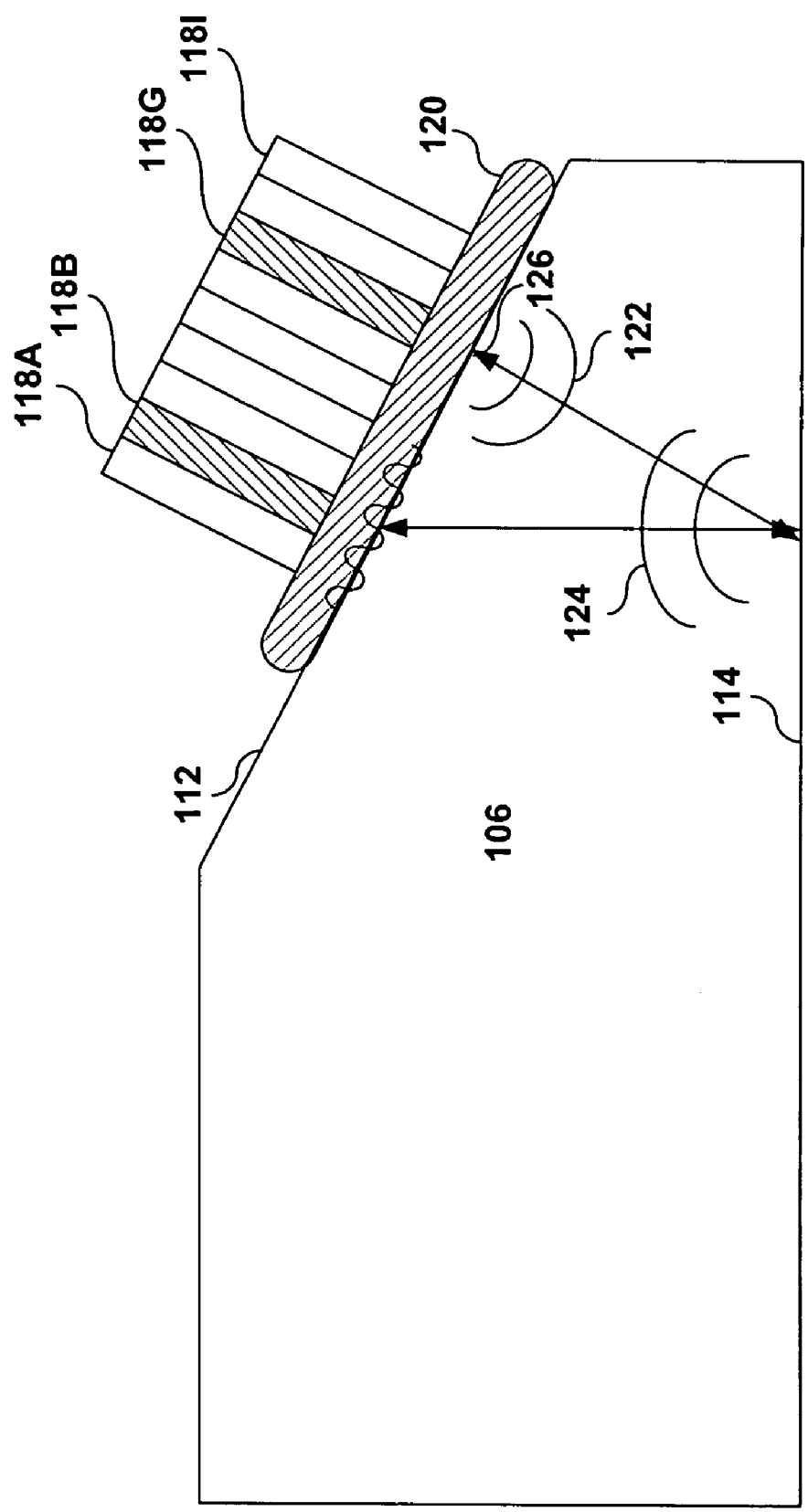
FIG. 4 illustrates the use of an array of piezoelectric transducers to generate and detect ultrasonic displacements in an object having non-parallel surfaces.

FIG. 4 illustrates a solution to the non-parallel surfaces problem. Here, instead of a single piezoelectric transducer 118, an array of transducers 118A-I, are employed. The emitting transducer and detecting transducer may differ as illustrated by transducer 118G and 118B. This does not reduce the normalcy requirements and still requires that the transducer be physically coupled with acoustic couplant 120 to remote target 106. This physical coupling makes the inspection of complex surfaces difficult and time consuming.

Figure 5:
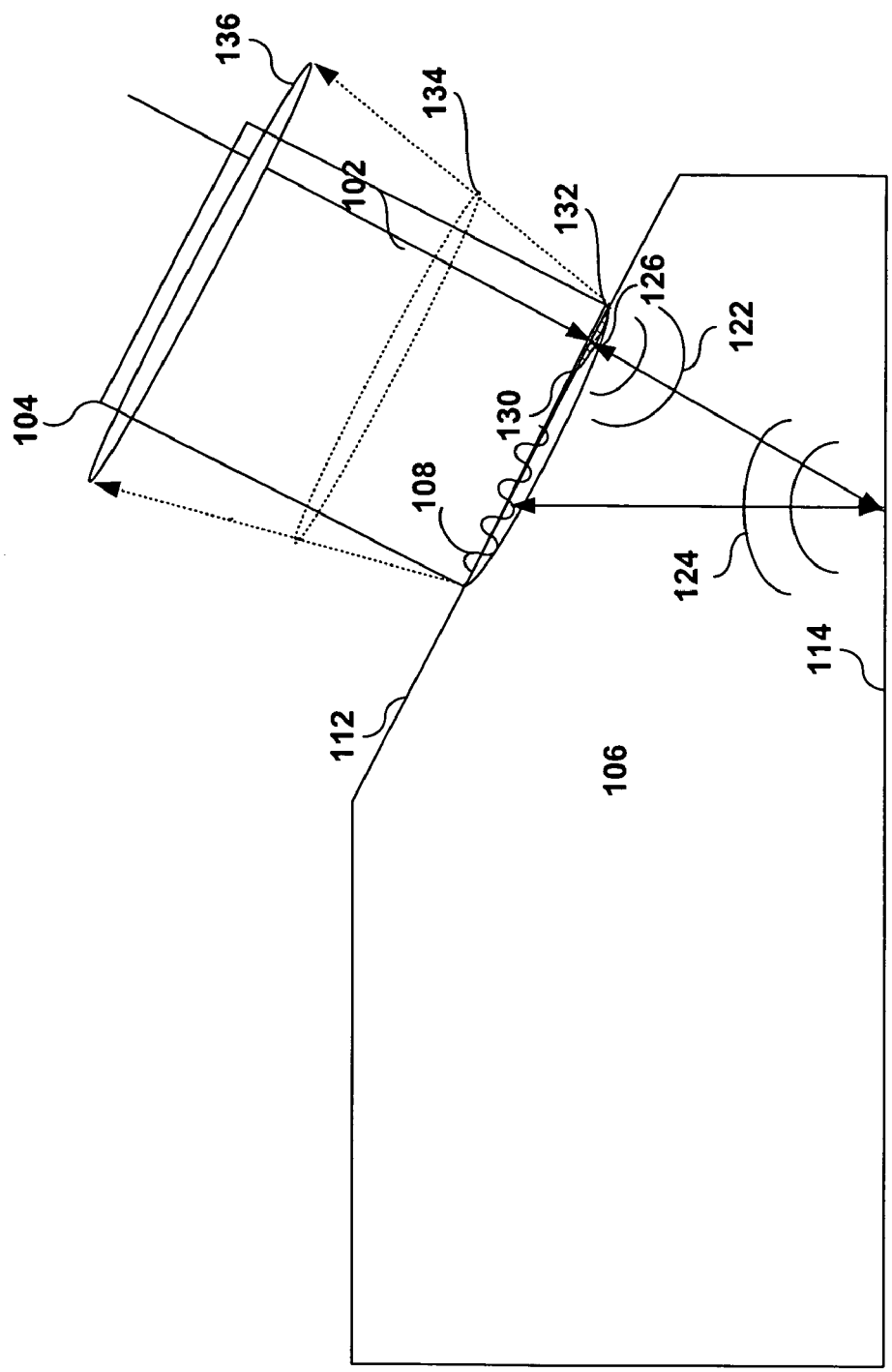
FIG. 5 illustrates the use of generation laser beam and a detection laser beam to generate and detect laser ultrasonic displacements in accordance with an embodiment of the present invention.
Figure 6:
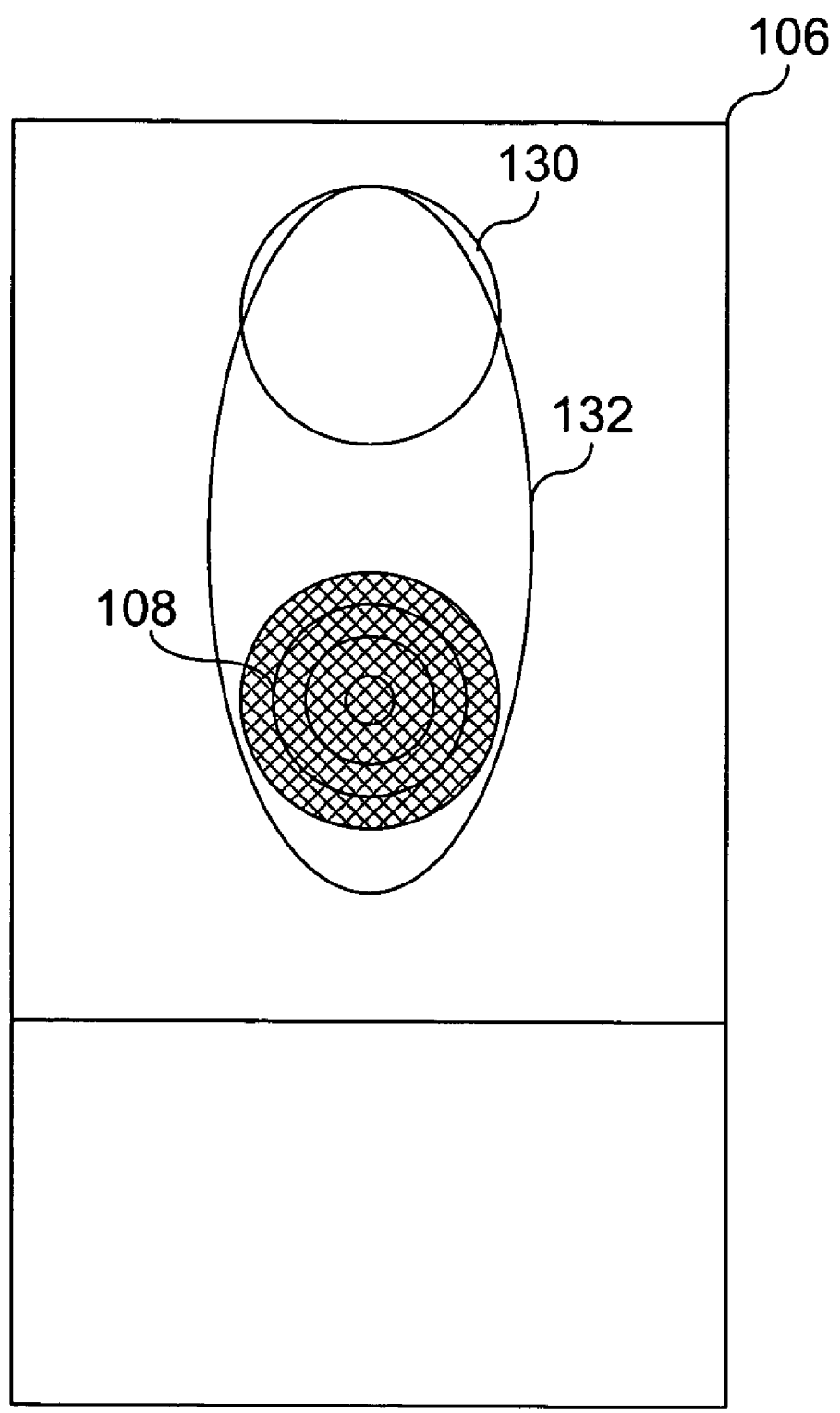
FIG. 6 provides a top down view of the generation field, detection field, and field of view of collection optics to generate and detect ultrasonic displacements in an object having non-parallel surfaces in accordance with an embodiment of the present invention.

FIGS. 5 and 6 provide a solution where the two incoming laser beams have overlapping fields of view within which laser ultrasonic displacement are both generated and detected. These fields may overlap but do so in such a way that the detection laser beam illuminates a field sufficiently large that ultrasonic displacements 108 may produce phase-modulated light 110 which may be collected by collection optics 136.

In FIG. 5, the problem of non-parallel surfaces within remote target 106 is addressed. A laser ultrasonic inspection system is used that employs a generation laser beam 102 and a detection laser beam 104. In this case, the field of view of the detection laser is expanded in order to encompass those locations within which ultrasonic displacements 108 may occur. Generation laser beam 102 is directed to a point on the surface of remote target 106. Exterior surface 112, as shown here, is not parallel with interior surface 114. The generation laser beam illuminates a generation field 130 from which an ultrasonic wave 122 is produced. This ultrasonic wave may be reflected by discontinuities, boundaries, or other interior surfaces within target 106. As shown here, ultrasonic waves 122 are reflected off of the back wall or interior surface 114 of remote target 106 to produce reflected wave 124. Because surfaces 112 and 114 are not parallel, reflected wave 124 will not return along the path of initial wave 122. A propagation direction of ultrasonic wave 124 is determined by the geometry and acoustic properties of ultrasonic wave 122 and remote target 106. Ultrasonic displacements 108 are produced at a second location away from the point of origin 126. Here, the field of view of detection laser beam 104 illuminates a larger area, i.e., detection field 132. Similarly, collection optics may be directed to capture scattered laser light produced by the interaction of laser beam 104 and ultrasonic displacements 108. The shape and exact location of the detection field associated with detection laser 104 may be optimized based on an expected second location where ultrasonic displacements 108 are expected to occur. This expected location may be calculated based on known dimensions and acoustic properties of remote target 106.

Typically, parts with non-parallel surfaces will have some symmetry with a knowledge of where the highest level of non-parallelism will be. For example, a semi-cylindrical shape that is thinner on the edges and thicker in the center will exhibit the highest level of non-parallelism on the edges. One embodiment allows the laser beams to be oriented at a point on the part where the non-parallelism is the highest. Then the detection laser is manually or automatically adjusted until the detection beam position and shape result in an acceptable signal. The system can be modified as the scan progresses knowing the symmetry of the part.

FIG. 6 provides a top down view of remote target 106 and generation field 130, detection field 132, and ultrasonic displacements 108. Here, detection field 132 is an ellipse that substantially overlaps both generation field 130 and ultrasonic displacements 108.

The sizes of the detection field and collection field may differ from that of the generation field. The sizes and relative positions of the detection field, collection field, and generation field may be determined according to the sample dimensions in the area to be inspected. Additionally, the optics associated with the illumination or detection laser and the collection optics may be controlled dynamically to alter the size and position of the field of view associated with the detection laser and the collection optics in order to maintain ultrasonic displacements 108 within the detection field and collection field. The required size and location of detection and collection field(s) can be calculated according to the geometrical dimensions, and acoustic properties of an area to be inspected. Since the sample may have a varied thickness, the arrival position of the back wall echo relative to the generation spot may vary. Some embodiments may dynamically reposition the detection field and collection field on ultrasonic displacements 108. Alternatively, the detection and collection field(s) can be expanded to ensure that the ultrasonic displacements 108 are within a detection field and collection field. Overexpansion of the detection field and collection field may result in reduced signal-to-noise ratio (SNR). Therefore, it is important to match the detection field and collection field with the position of the ultrasonic displacements 108.

In addition to providing the ability to inspect composite materials having non-parallel surfaces, normalcy requirements may be reduced by matching the detection field and orthogonal collection field with the location of the ultrasonic displacements. This reduces or eliminates the need for complex robotics used in prior art systems to keep a physical transducer both coupled and normal to the sample surface at all times. The need for complex arrays of transducers is also eliminated. These benefits result in improved ultrasonic inspection tasks.

Figure 7:
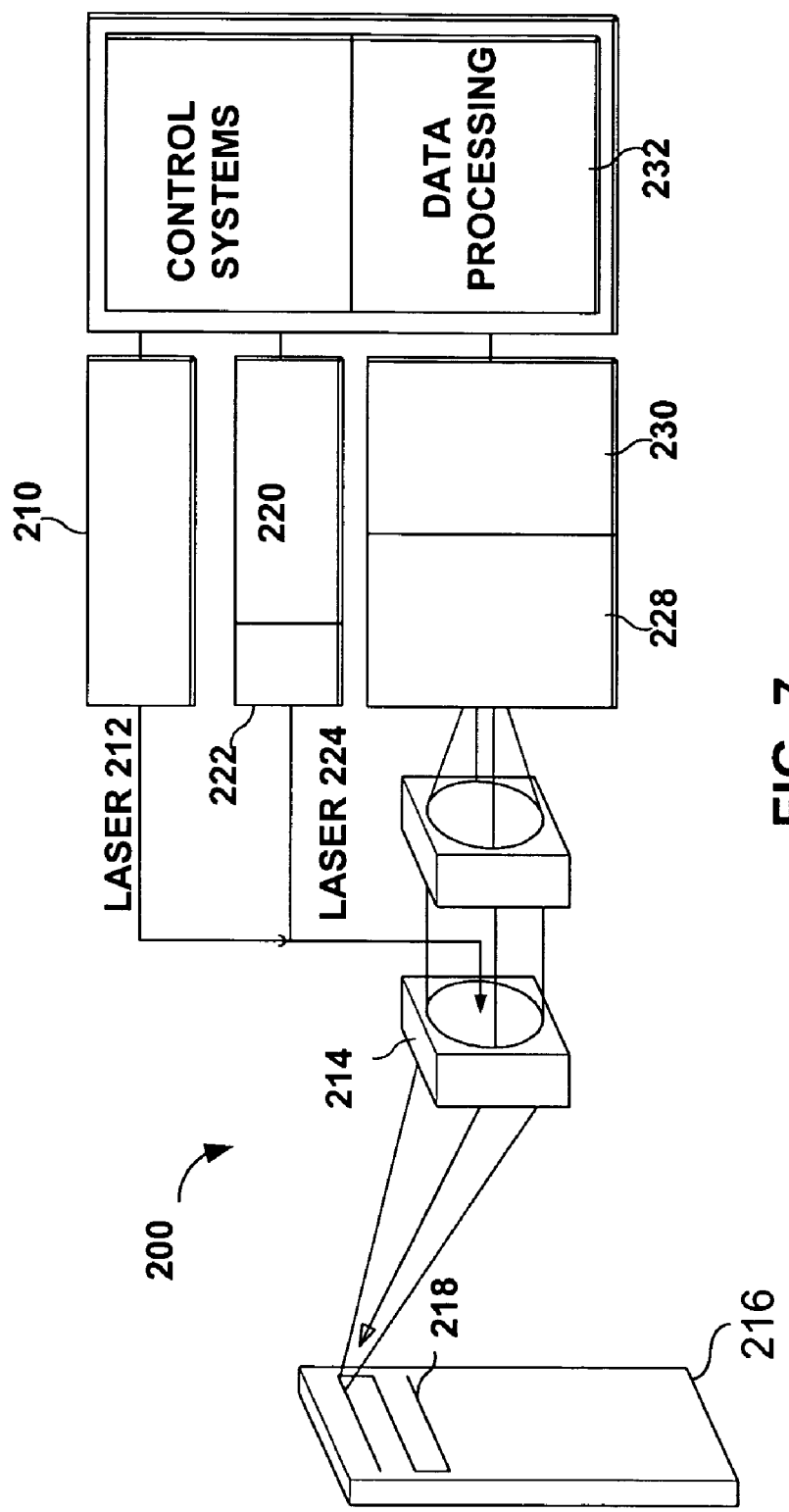
FIG. 7 provides a block diagram to show the basic components of laser ultrasound system in accordance with an embodiment of the present invention.

FIG. 7 provides a block diagram with the basic components for performing ultrasonic laser testing. Generation laser 210 produces laser beam 212 which optical assembly 214 directs to target 106. As shown, optical assembly 214 includes a scanner or other like mechanism that moves laser beam 212 along a scan or test plan 218. Optical assembly 214 may include visual cameras, depth cameras, range detectors, narrowband cameras or other like optical sensors known to those having skill in the art. These optical sensors each may require calibrations prior to performing an inspection. This calibration verifies the ability of the system to integrate information gathered by various sensors. Generation laser 210 produces an ultrasonic wave 108 within target 216.

The ultrasonic wave is the result of thermo-elastic expansion of the composite material as the material absorbs the generation laser beam. Composite material 106 readily absorbs generation laser beam 212 without ablating or breaking down. Higher powered generation lasers are not necessarily preferred to overcome SNR issues as these can result in ablation. In other embodiments, depending on the material being tested, some ablation may be acceptable in order to increase the SNR of the detected signal. Generation laser beam 212 has appropriate pulse duration to induce ultrasonic surface deformations. For example, a transverse-excited atmospheric (TEA) $CO_2$ laser can produce a 10.6 micron wavelength beam for a 100 nanosecond pulse. The power of the laser must be sufficient to deliver, for example, a 0.25 joule pulse to the target, which may require a 100 watt laser operating at a 400 Hz pulse repetition rate. Generation laser beam 212 absorbs as heat into the target surface thereby causing thermo-elastic expansion without ablation.

Illumination laser 220 operation pulsed mode or continuous wave mode as to not induce ultrasonic displacements. For example, an Nd:YAG laser can be used. The power of this laser must be sufficient to deliver, for example, a 100 milli-joule, 100 micro-second pulse, which may require a one kilo-watt laser. Illumination laser 220 generates detection laser beam 222. Illumination laser 220 includes or optically couples to filtering mechanism 224 to remove noise from detection laser beam 224. Optical assembly 214 directs illumination laser beam 224 to the surface of composite material 106 which scatters and/or reflects detection laser beam 224. Resultant phase-modulated light is collected by collection optics 226. As shown here, scattered and/or reflected illumination laser travels back through optical assembly 214.

Optical processors 228, such as interferometer 230, process the phase-modulated light to produce a signal containing information representative of the ultrasonic displacements at the surface of composite material 216. Data and signal processors provide input to control system 232 to coordinate operation of the laser ultrasound system components. More specifically, control system 232 may drive the optical components to ensure that detection laser illuminates the ultrasonic displacements and that the collection optics are operable to collect the phase-modulated light. When an optical probe, such as that described in U.S. patent application Ser. No. 11/018,994, entitled "SYSTEM AND METHOD TO DECREASE PROBE SIZE FOR IMPROVED LASER ULTRASOUND DETECTION" which is hereby incorporated by reference, is employed, different angle terminated fiber combinations may be employed to ensure that the detection laser illuminates the ultrasonic displacements with the field of view of the collection optics. The optical and signal processors performed also provide information about the internal structure of the target. This data may be presented visually or by other means known to those having skill in the art.

Data and signal processing may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. The memory stores, and data processing and control system 232 executes, operational instructions corresponding to at least some of the steps and/or functions as will be illustrated in FIG. 8.

Figure 8:
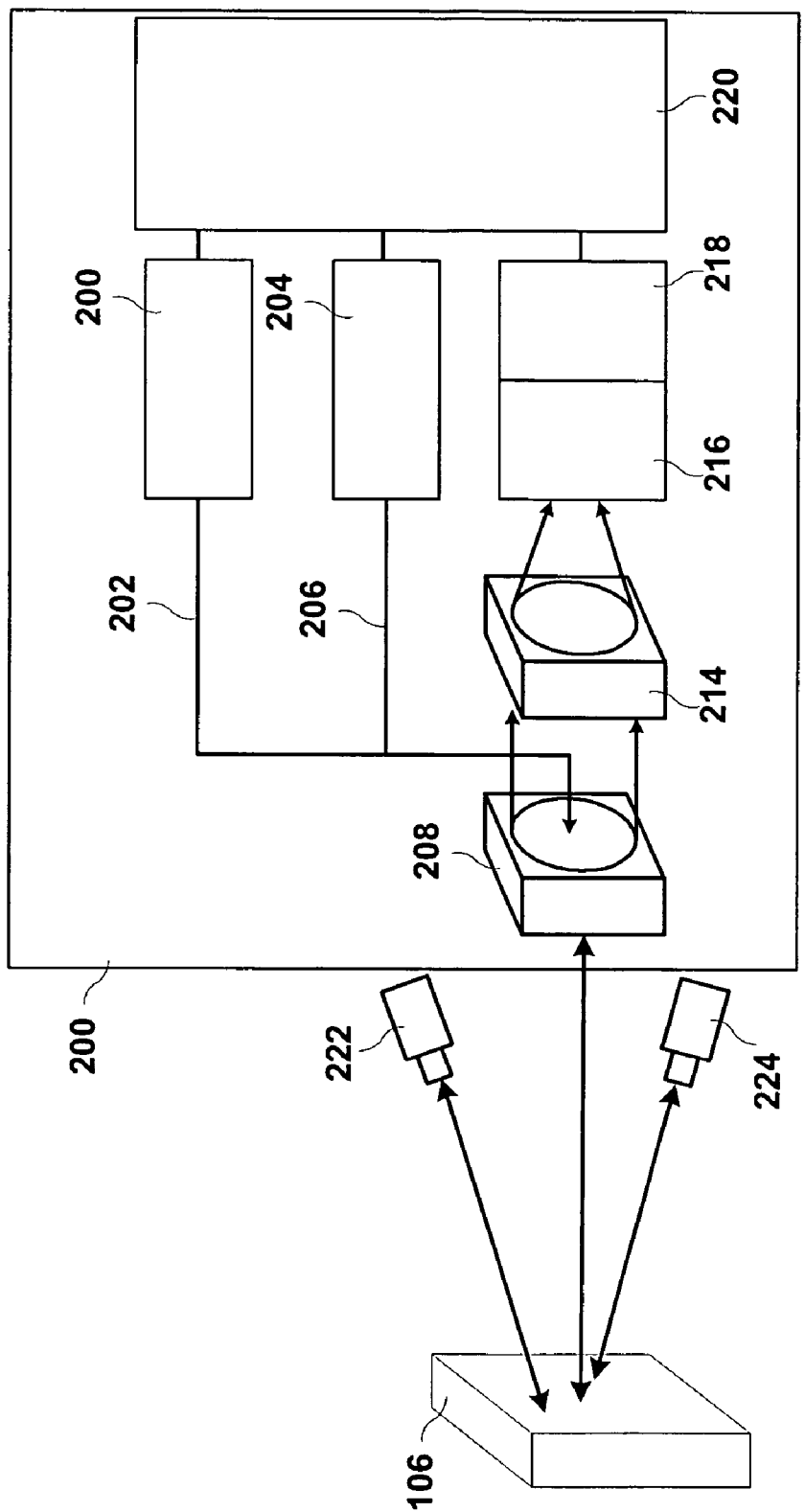
FIG. 8 provides a block diagram to show the basic components of laser ultrasound system in accordance with another embodiment of the present invention.

FIG. 8 illustrates a laser ultrasonic inspection system having additional sensors such as optical camera 222 and range camera 224. Optical assembly 208 of laser ultrasonic inspection 200, optical camera 222 and range camera 224 are focused on remote target 106. Information from laser ultrasonic inspection 200, optical camera 222, range camera 224, narrowband cameras, and/or other like optical sensors are combined in control module 220 to identify the size and shape of remote target 106. This information may be used to determine where the detection laser and collection optics are to be focused on the surface of target 106. Additionally, computer modeling information associated with the remote target may be used to control the detection laser and collection optics. The system may compare the measured results to the known information associated with the target. This allows information gathered from various sensors to be properly correlated while minimizing location errors.

Figure 9:
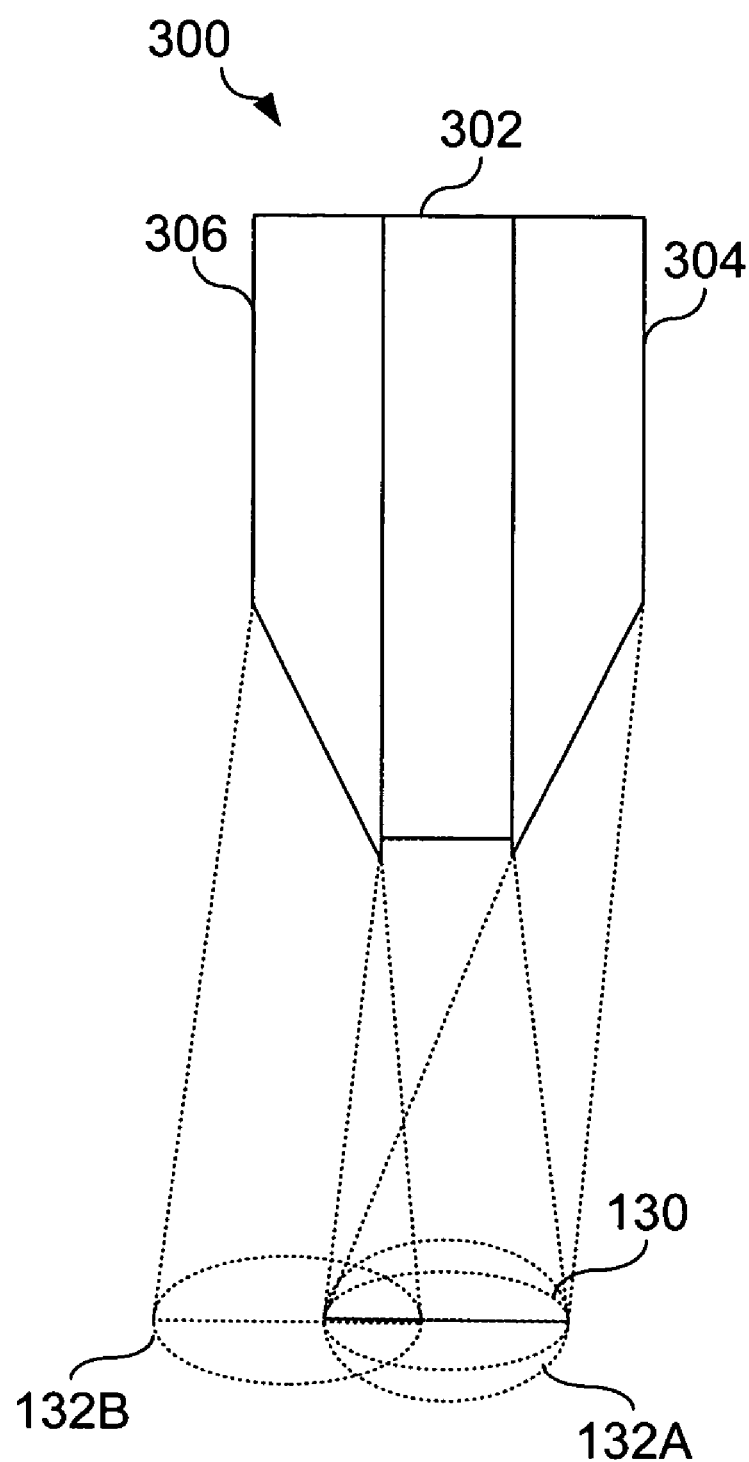
FIG. 9 illustrates a compact optical probe having a number of fibers to generate and detect ultrasonic displacements in an object having non-parallel surfaces in accordance with an embodiment of the present invention.

FIG. 9 depicts compact optical probe 300 having multiple angle-terminated optical fibers. Compact optical probe 300 transports detection laser beam 104 and collected phase-modulated light 110 within angle terminated fibers having a common field of view such as that indicated by ellipses 132A and 132B. The generation laser may be transported by the fiber bundle as well to the surface of the remote target with ellipse 130, which may or may not overlap with the ellipses 132A and 132B. Terminating the optical fiber at specific angles allows the optical axis of the individual optical fibers to be adjusted relative to the longitudinal axis of the optical fiber. Multiple angle-terminated optical fibers can be incorporated in a compact optical probe in such a manner that the fields of view of the optical fibers completely or nearly completely overlap. Detection and generation laser beam(s) are directed by the angle-terminated optical fibers of the compact optical probe.

The orientation and shape of the polished facets of each angle-terminated fiber may vary. The angle-terminated collection optical fibers may have facets or lenses that differ. Optical fibers 302, 304 and 306 have different facets that allow illumination or fields 132A and 132B respectively, to interact with the surface of the remote target as required by the reflection of ultrasonic waves within. Each facet may be created to maximize the optical efficiency for a particular application. A beam forming element, such as a lens, grating or other like device known to those skilled in the art, may be placed between the optical fibers and field of view. The various optical fibers may be angle terminated where each individual angle or facet may be chosen so that the spot seen by each fiber overlaps the ultrasonic displacements at the surface of the target for specialized applications. This may allow the distance between the optical probe and the remote target to vary. Several configurations are possible when optical fiber positions in the head and tip angles or facets are calculated to maximum optical efficiency for each particular application. Additionally these fibers may perform various functions. For example one collection fiber could be replaced and used as a generation fiber that is angle-terminated. Other configurations containing even more fibers can also be conceived. Such configurations might contain fibers having several different termination angles in order to make the field of view overlap as much as possible. It is also possible that the fibers be terminated by a curved surface instead of a flat angled surface.

Figure 10:
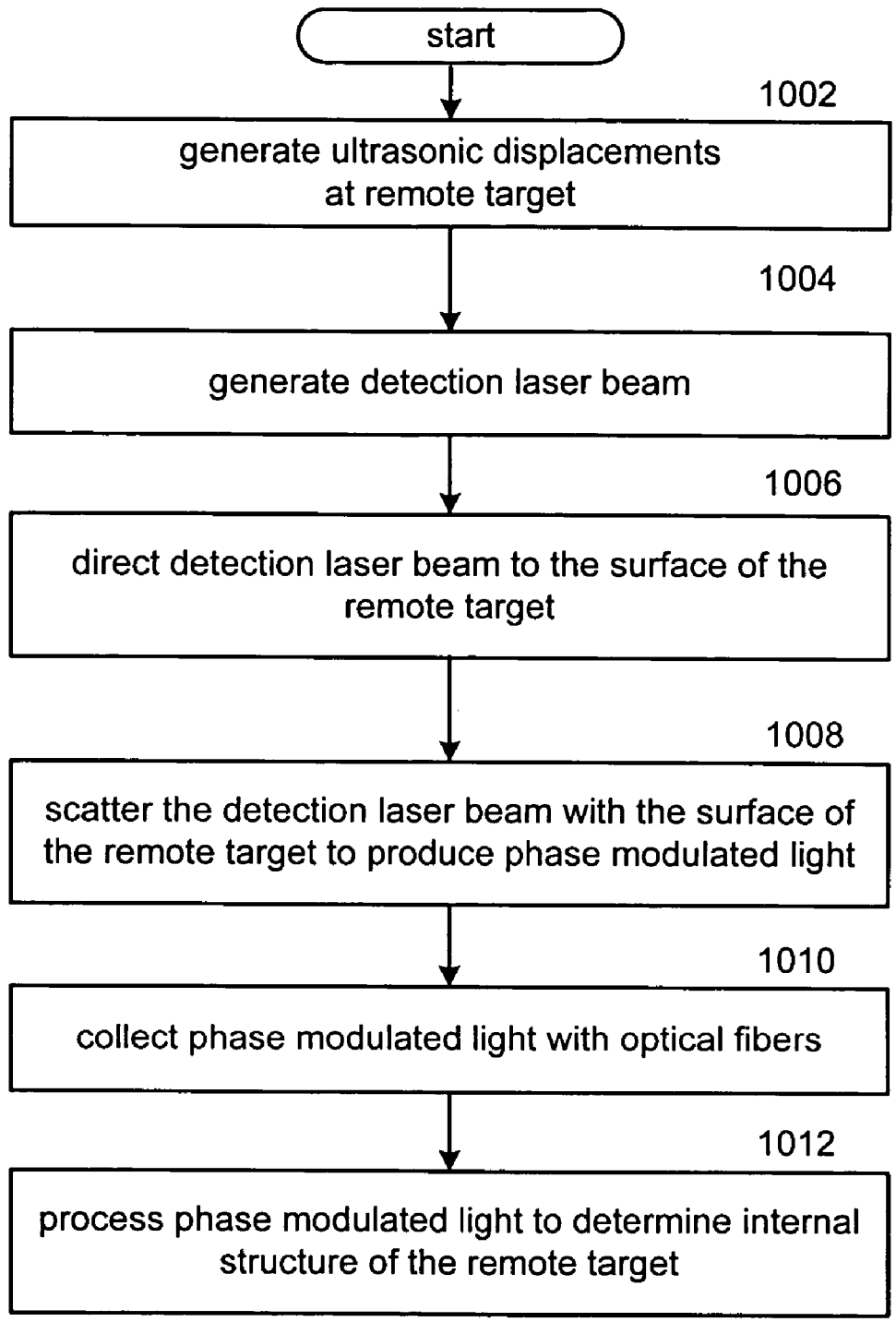
FIG. 10 provides a logic flow diagram illustrating a method to perform laser ultrasonic in accordance with an embodiment of the present invention.

FIG. 10 provides a logic flow diagram illustrating a method to perform laser ultrasonic inspections of a remote target, such as a composite material work piece. This composite material work piece may be used in the fabrication of aircraft of other structures. An ultrasonic wave is generated at a first location within a generation field of a generation laser beam directed to an exterior surface of the remote target in step 1002. In step 1004, a detection laser beam is generated for delivery to the surface of the remote target in step 1006. The detection laser beam may be delivered to a detection field that may not necessarily overlap the generation field of the generation laser beam. Common optics, a compact optical probe, or other like optical assemblies may be used to transport the generation laser, detection laser, and scattered phase-modulated light. In step 1008, the remote target then scatters the detection laser beam with ultrasonic surface displacements at its surface to produce phase-modulated light. The phase-modulated light is collected at step 1010. Then the phase-modulated light is processed in step 1012 to obtain data representative of the ultrasonic surface displacements at the surface. This data may be further processed to determine the internal structure of the remote target. This data may be correlated with that of other sensors for further analysis and visualization.

In summary, the present invention provides a method to detect and generate ultrasonic displacements at a remote target for ultrasonic inspection. This involves generating an ultrasonic wave at a first location on an upper surface of the remote target. This ultrasonic wave is reflected from interior surfaces within the remote target wherein the reflected ultrasonic wave produces ultrasonic displacement at a second location on the upper surface of the remote target. These exterior and interior surfaces are not necessarily parallel. A detection laser beam is generated and directed to the second location on the upper surface of the remote target. Here, the detection laser beam is scattered by the ultrasonic displacements to produce phase-modulated light. This phase-modulated light is collected and processed to obtain data representative of the ultrasonic surface displacements. Further, these ultrasonic displacements, when processed, will yield inspection information associated with the interior of the remote target.

In operation the present invention allows laser ultrasonic test equipment to be used in a wider range of environments while testing more complex surfaces, complex parts and materials or surfaces within limited access areas. The present invention also allows existing laser ultrasound equipment to be modified to test more complex surfaces or surfaces within limited access areas without replacing the existing detection laser, an expensive component in the laser ultrasound system.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention has been described in detail, it should be understood that various changes, substitutions and alterations can be made hereto without departing from the spirit and scope of the invention as defined by the appended claims.

What is claimed is:

1. A method to generate and detect ultrasonic surface displacements at a remote target comprising:
    generating an ultrasonic wave at a first location on an upper surface of the remote target with a generation laser beam directed at the first location, wherein the generation laser beam forms a generation field on the remote target;
    reflecting the ultrasonic wave from an interior surface of the remote target, wherein the reflected ultrasonic wave produces ultrasonic displacements at a second location on the upper surface of the remote target;
    generating a detection laser beam; directing the detection laser beam at the upper surface of the remote target wherein the detection laser beam forms a detection field on the target and wherein the detection field overlaps the generation field and the second location;
    scattering the detection laser beam with the ultrasonic displacements at the second location on the upper surface of the remote target to produce phase-modulated light;
    collecting the phase-modulated light;
    processing the phase-modulated light to: obtain data representative of the ultrasonic surface displacements at the surface; and inspection information representative of the interior of the remote target, and
    visually presenting at least a portion of the data.

2. The method of claim 1, further comprising determining the second location from dimensions of the remote target.

3. The method of claim 1, wherein a detection field of the detection laser beam substantially overlaps both the first location and the second location.

4. The method of claim 1, wherein a detection field of the detection laser beam substantially overlaps a generation field at the first location to be illuminated by the generation laser beam.

5. The method of claim 1, wherein the upper surface and interior surface are not parallel.

6. The method of claim 1, wherein the interior surface is not orthogonal to the generated ultrasonic wave.

7. The method of claim 1, wherein a compact optical probe having a plurality of angle terminated fibers directs the generation laser beam to the remote target; direct the detection laser beam to the remote target; and collect the phase-modulated light.

8. The method of claim 2, wherein the dimensions of the remote target are determined from a computer model of the remote target.

9. The method of claim 1, wherein the dimensions of the remote target are determined from sensors inputs.

10. The method of claim 1, wherein the second location comprises a detection spot, and wherein determining a location and shape of the detection spot on the remote target comprises repeatedly changing the shape and relative location of the detection spot in order to optimize an ultrasonic signal within the phase modulated light.

11. A laser ultrasonic inspection system operable to detect ultrasonic displacements at a remote target, comprising:
    a generation laser source to generate a detection laser beam;
    a first optical assembly that receives and directs the generation laser beam to the remote target where the generation laser beam generates an ultrasonic wave originating from a first location on an upper surface of the remote target, wherein the generation laser beam forms a generation beam field on the target;
    a detection laser source to generate a detection laser beam;
    a second optical assembly that receives and directs the detection laser beam to the remote target where ultrasonic displacements at a second location on the surface of the remote target scatter the detection laser beam to produce phase-modulated light, and wherein the detection laser beam forms a detection laser beam field on the target that overlaps the generation beam field and the second location;
    collection optics to collect the phase-modulated light;
    an interferometer to process the phase-modulated light and generate at least one output signal; and
    a processor to data representative of the ultrasonic surface displacements at the surface; and inspection information representative of the interior of the remote target.

12. The laser ultrasonic inspection system of claim 11, wherein: the generation laser beam illuminates a generation field substantially at the first location; and the detection laser beam illuminates a detection field substantially at the second location; and collection optics collect the phase-modulated light from a collection field substantially at the second location.

13. The laser ultrasonic inspection system of claim 11 further comprising an optical control system to position fields of view of the detection laser beam and collection optics to the second location, and wherein the optical control system determines the second location based on dimensions of the remote target and the first location.

14. The laser ultrasonic inspection system of claim 13, further comprising inspection sensors for determining the dimensions and orientation of the remote target.

15. The laser ultrasonic inspection system of claim 13, further comprising memory for storing computer models of the remote target from which the dimensions are determined.

16. The laser ultrasonic inspection system of claim 11, wherein a detection field of the detection laser beam substantially overlaps a generation field at the first location to be illuminated by the generation laser beam.

17. The laser ultrasonic inspection system of claim 11, wherein the upper surface and interior surface of the remote target are not parallel.

18. The laser ultrasonic inspection system of claim 11, wherein the interior surface is not orthogonal to the generated ultrasonic wave.

19. The laser ultrasonic inspection system of claim 11, further comprising a compact optical probe having a plurality of angle terminated fibers, wherein said optical probe directs the generation laser beam to the remote target; directs the detection laser beam to the remote target; and collects the phase-modulated light.

20. The laser ultrasonic inspection system of claim 11, wherein the remote target comprises a composite materiel.

21. The laser ultrasonic inspection system of claim 11, wherein the remote target comprises a composite materiel having non parallel outer surfaces.

22. A laser ultrasonic inspection system operable to inspect an object fabricated with composite materials, comprising:
   a plurality of sensors to detect, locate and measure dimensions of the object;
   a generation laser source to generate a detection laser beam;
   a first optical assembly that receives and directs the generation laser beam to illuminate a generation field substantially located at a first location on an outer surface of the object, wherein the generation laser beam generates an ultrasonic wave originating from the first location on the outer surface of the object;
   a detection laser source to generate a detection laser beam;
   a second optical assembly that receives and directs the detection laser beam to illuminate a detection field that encompasses the generation field and a second location on the surface of the object, wherein ultrasonic displacements at the second location on the surface of the object scatter the detection laser beam to produce phase-modulated light, wherein the ultrasonic displacements are produced by reflecting the ultrasonic wave from an interior surface within the object to the second location; collection optics to collect the phase-modulated light, wherein the collection optics collect the phase-modulated light from a collection field substantially located at the second location;
   an interferometer to process the phase-modulated light and generate at least one output signal; and
   a processor obtain data representative of the ultrasonic surface displacements; and
   inspection information representative of the interior of the object.

23. The laser ultrasonic inspection system of claim 22, further comprising an optical control system to position fields of view of the detection laser beam and collection optics to the second location, and wherein the optical control system determines the second location based on dimensions of the object and the first location.

24. The laser ultrasonic inspection system of claim 23, further comprising memory operable to store computer models of the object from which the dimensions are determined.

25. The laser ultrasonic inspection system of claim 22, wherein the interior surface is not orthogonal to the generated ultrasonic wave.

26. The laser ultrasonic inspection system of claim 22, further comprising a compact optical probe having a plurality of angle terminated fibers fibers wherein said optical probe directs the generation laser beam to the object; directs the detection laser beam to the object; and collects the phase-modulated light.

* * * * *